United States Patent [19]

Koppel

[11] 4,048,160

[45] Sept. 13, 1977

[54] PROCESS FOR PREPARATION OF 7-ALKOXY-3-BROMOMETHYLCEPHEMS

[75] Inventor: Gary A. Koppel, Indianapolis, Ind.

[73] Assignee: Eli Lilly and Company, Indianapolis, Ind.

[21] Appl. No.: 669,366

[22] Filed: Mar. 22, 1976

[51] Int. Cl.$^2$ .................. A61K 31/545; C07D 501/04
[52] U.S. Cl. ...................................... 544/21; 424/246
[58] Field of Search .................................. 260/243 C

[56] References Cited

U.S. PATENT DOCUMENTS

| 3,637,678 | 1/1972 | Webber et al. | 260/243 C |
| 3,658,799 | 4/1972 | Eardley et al. | 260/243 C |
| 3,705,897 | 12/1972 | Murphy | 260/243 C |

FOREIGN PATENT DOCUMENTS 1,407,348   9/1975   United Kingdom ............. 260/243 C

OTHER PUBLICATIONS

Koppel et al., JACS, 95 2403 (1973).
Karady et al., Tetra Hedron Letters 30 2625 (1974).

Primary Examiner—Nicholas S. Rizzo
Attorney, Agent, or Firm—Steven R. Lammert; Everet F. Smith

[57] ABSTRACT

7-Alkoxy-3-bromomethyl-3-cephems are provided by reacting a 3-methylenecepham with an alkali metal salt of a lower primary alcohol in the presence of a positive brominating agent at a temperature ranging from about −80° to about 0° C. The 3-bromomethylcephems provided by this invention are useful intermediates for the preparation of known cephalosporin antibiotics.

12 Claims, No Drawings

PROCESS FOR PREPARATION OF 7-ALKOXY-3-BROMOMETHYLCEPHEMS

BACKGROUND OF THE INVENTION

This invention relates to the cephalosporin class of antibiotics. In particular, this invention relates to a process for preparing 7-alkoxy-3-bromomethyl-3-cephem compounds from 3-methylenecephams.

3-Halomethylcephems are known in the cephalosporin art and have proved to be useful intermediates for the preparation, via nucleophilic displacement of the halogen atom, of many related cephalosporin antibiotic compounds. 3-Halomethylcephems have heretofore been available by allylic halogenation of the corresponding desacetoxycephalosporin compounds (U.S. Pat. Nos. 3,637,678 and 3,705,897) and by halogenation of the corresponding desacetylcephalosporins (U.S. Pat. No. 3,658,799). More recently 3-halomethylcephams have been prepared by cleavage of 3-acetoxymethyl and 3-carbamoyloxymethyl cephems with hydrohalic acids [S. Karady, T. Y. Cheng, S. H. Pines and M. Sletzinger, *Tetrahedron Letters*, 30, 2625 (1974)].

It is an object of this invention to provide a novel process for the preparation of 7-alkoxy-3-bromomethylcephems from 3-methylenecephams.

SUMMARY OF THE INVENTION

This invention is directed to a process for preparing 7-alkoxy-3-bromomethylcephems represented by the general formula

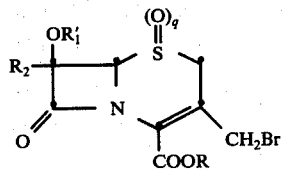

by reacting in an inert organic solvent a 3-methylenecepham of the formula

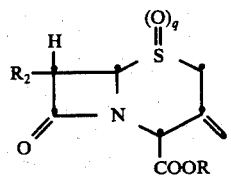

with an alkali metal salt of a primary $C_1$–$C_7$ alcohol in the presence of a positive brominating agent at sub-ambient temperatures, preferably between −80° and −20° C. wherein in the above formulae $q$ is 1 or 0 representing a sulfoxide or sulfide respectively; R is a carboxylic acid protecting group, preferably one which can be readily removed so as to provide the carboxylic acid form of the 3-bromomethylcephem or compounds derived therefrom; $R_1'$ is lower alkyl; and $R_2$ is preferably an acylamino group, representing a wide variety of known penicillin and cephalosporin side chains including phenylacetamido, phenoxyacetamido, 2-thienylacetamido, phenylglycylamido, mandelamido, and like groups.

DETAILED DESCRIPTION OF THE INVENTION

This invention provides a process for preparing a 7-alkoxy-3-bromometylcephem compound of the formula

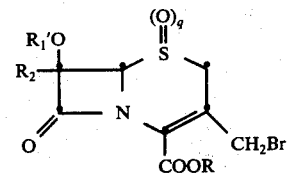

which comprises reacting a compound of the formula

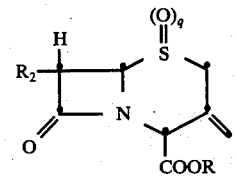

with from about 4 to about 8 equivalents of an alkali metal salt of a $C_1$–$C_7$ primary alcohol of the formula $R_1'OH$ in the presence of about 4 to about 8 equivalents of a positive brominating agent selected from the group consisting of bromine, DBU hydrobromide perbromide, iodine monobromide and tert-butyl hypobromite in an inert organic solvent at a temperature of −80° to about 0° C. wherein in the above formulae $q$ is 1 or 0;
R is a carboxylic acid protecting group;
$R_1'$ is $C_1$ to $C_6$ primary alkyl or benzyl;
$R_2$ is an amido group of the formula

wherein $R_3$ is
a. hydrogen, $C_1$–$C_3$ alkyl, halomethyl, 3-(2-chlorophenyl)-5-methylisoxazol-4-yl or 4-protected amino-4-protected carboxybutyl;
b. benzyloxy, 4-nitrobenzyloxy, 2,2,2-trichloroethoxy, tert-butoxy, or 4-methoxybenzyloxy;
c. the group —R″ wherein R″ is 1,4-cyclohexadienyl, phenyl or phenyl substituted with 1 or 2 substituents independently selected from the group consisting of halo, protected hydroxy, nitro, cyano, trifluoromethyl, $C_1$–$C_3$ alkyl, and $C_1$–$C_7$ alkoxy;
d. an arylalkyl group of the formula

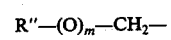

wherein R″ is as defined above, and $m$ is 0 or 1;
e. substituted arylalkyl group of the formula

wherein R‴ is R″ as defined above, 2-thienyl or 3-thienyl, and W is protected hydroxy or protected amino; or
f. a heteroarylmethyl group of the formula

R''''—CH$_2$— wherein R'''' is 2-thienyl, 3-thienyl, 2-furyl, 2-thiazolyl, 5-tetrazolyl, 1-tetrazolyl, or 4-isoxazolyl;

with the limitation that when R''' or R'''' is 2-thienyl, 3-thienyl, or 2-furyl the reaction is carried out at a temperature below about −40° C. and a halogen quenching agent is added before the reaction mixture is allowed to warm above about 0° C.

In the foregoing definition of the process of the present invention the term "C$_1$-C$_3$ alkyl" refers to methyl, ethyl, n-propyl or isopropyl. The term "C$_1$-C$_7$ alkoxy" refers to such groups as methoxy, ethoxy, n-propoxy, isopropoxy, n-butoxy, tert-butoxy, cyclohexyloxy, benzyloxy and like groups. The term "C$_1$-C$_6$ primary alkyl" refers to methyl, ethyl, n-propyl, n-butyl, isobutyl, n-pentyl and n-hexyl. Illustrative of an "alkali salt of a primary C$_1$-C$_7$ alcohol" are lithium methoxide, sodium ethoxide, potassium ethoxide, lithium butoxide, sodium benzyloxide, and sodium n-propoxide.

When in the above definition R'' represents a substituted phenyl group, R'' can be a mono or disubstituted halophenyl group such as 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl and the like; a protected hydroxy phenyl group such as 4-benzyloxyphenyl, 3-benzyloxyphenyl, 4-tert-butoxyphenyl, 4-tetrahydropyranyloxyphenyl, 4-(4-nitrobenzyloxy)phenyl, 2-phenacyloxyphenyl, 4-benzhydroxyphenyl, 4-trityloxyphenyl and like groups; a nitrophenyl group such as 3-nitrophenyl or 4-nitrophenyl; a cyanophenyl group, for example, 4-cyanophenyl; a mono or dialkyl substituted phenyl group such as 4-methylphenyl, 2,4-dimethylphenyl, 2-ethylphenyl, 4-isopropylphenyl, 4-ethylphenyl, 3-n-propylphenyl and the like; a mono or dialkoxyphenyl group, for example, 2,6-dimethoxyphenyl, 4-methoxyphenyl, 3-ethoxyphenyl, 4-isopropoxyphenyl, 4-tert-butoxyphenyl, 3-ethoxy-4-methoxyphenyl and the like. Also, R'' represents disubstituted phenyl groups wherein the substituents can be different for example, 3-methyl-4-methoxyphenyl, 3-chloro-4-benzyloxyphenyl, 2-methoxy-4-bromophenyl, 4-ethyl-2-methoxyphenyl, 3-chloro-4-nitrophenyl, 2-methyl-4-chlorophenyl and like disubstituted phenyl groups bearing different substituents.

The term "protected amino" as employed in the above definition has reference to an amino group substituted with one of the commonly employed amino blocking groups such as the tert-butoxycarbonyl group (t-BOC); the benzyloxycarbonyl group, the 4-methoxybenzyloxycarbonyl group, the 4-nitrobenzyloxycarbonyl group, or the 2,2,2-trichloroethoxycarbonyl group. Like conventional amino protecting groups such as those described by J. W. Barton in "Protective Groups in Organic Chemistry," J. F. W. McOmie, Ed., Plenum Press, New York, N.Y., 1973, Chapter 2 shall be recognized as suitable.

The term "protected hydroxy" has reference to the readily cleavable groups formed with an hydroxyl group such as the formyloxy group, the chloroacetoxy group, the benzyloxy group, the benzhydryloxy group, the trityloxy group, the 4-nitrobenzyloxy group, the trimethylsilyloxy group, the phenacyloxy group, the tert-butoxy group, the methoxymethoxy group, the tetrahydropyranyloxy group, and the like. Other hydroxy protecting groups, including those described by C. B. Reese in "Protective Groups in Organic Chemistry", supra, Chapter 3 shall be considered as within the term "protected hydroxy" as used herein.

The term "protected carboxy" has reference to a carboxy group which has been protected by one of the commonly used carboxylic acid protecting groups employed to block or protect the carboxylic acid functionality while reactions involving other functional sites of the compound are carried out. Such protected carboxy groups are noted for their ease of cleavage by hydrolytic or by hydrogenolytic methods to the corresponding carboxylic acid. Examples of carboxylic acid ester protecting groups include methyl, tert-butyl, benzyl, 4-methoxybenzyl, C$_2$-C$_6$ alkanoyloxymethyl, 2-iodoethyl, 4-nitrobenzyl, diphenylmethyl (benzhydryl), phenacyl, p-halophenacyl, 2,2,2-trichloroethyl, succinimidomethyl, tri(C$_1$-C$_3$ alkyl)silyl and like ester forming moieties. Other known conventional carboxy protecting groups such as those described by E. Haslam in "Protective Groups in Organic Chemistry", supra, Chapter 5, shall be recognized as suitable. The nature of such ester forming groups is not critical so long as the particular ester formed therewith is stable under the reaction conditions described hereinafter. Preferred carboxylic acid ester protecting groups are tert-butyl, 4-methoxybenzyl, benzhydryl, 4-nitrobenzyl, and 2,2,2-trichloroethyl.

In the foregoing definitions, hydroxy, amino, and carboxy protecting groups are not exhaustively defined. The function of such groups is to protect the reactive functional groups during the preparation of the desired products and then be removed without disrupting the remainder of the molecule. Many such protective groups are well known in the art and the use of other groups equally applicable to the process and compounds of the present invention shall be recognized as suitable. Thus, there is no novelty or inventiveness asserted with regard to the protecting groups alluded to in this specification nor is it intended that the invention be limited by the groups specifically disclosed herein.

Likewise the nature of the side chain group R$_2$ is not critical to the process of the present invention, that is, the process of converting a 3-methylenecepham to a 3-bromomethylcephem. It should be noted, however, that some side chain groups, notably those containing a thienyl or furyl moiety, are particularly susceptible to halogenation on the heteroaryl group under reaction conditions within the scope of the present invention. As detailed hereinbelow, however, special precautions, including the use of halogen quenching agents preferably in conjunction with lower reaction temperatures, can be employed to minimize the possibility of concommitant side chain halogenation during the conversion to which the present process is directed. Since the side chains on the product of the process of this invention and on compounds derived therefrom are often subsequently cleaved, and the resulting nucleus esters then reacylated, possible side chain halogenation does not affect the utility of the process of this invention.

Representative of the acylamino group,

as defined hereinabove are formamido, acetamido, propionamido, butyramido, 2-pentenoylamino, chloroacetamido, bromoacetamido, 5-tert-butoxycarbonylamino-5-tert-butoxycarbonylvaleramido, and the like.

Illustrative of the particular acylamino group,

are benzamido, 2,6-dimethoxybenzamido, 4-chlorobenzamido, 4-methylbenzamido, 3,4-dichlorobenzamido, 4-cyanobenzamido, 3-bromobenzamido, 3-nitrobenzamido and the like.

Exemplary of the acylamino group

when $R_3$ is a group of the formula $R''(O)_mCH_2—$ and $m$ is O, are cyclohexa-1,4-dienylacetamido, phenylacetamido, 4-chlorophenylacetamido, 3-methoxyphenylacetamido, 3-cyanophenylacetamido, 3-methylphenylacetamido, 4-bromophenylacetamido, 4-ethoxyphenylacetamido, 4-nitrophenylacetamido, 3,4-dimethoxyphenylacetamido and the like; and when $m$ is 1, representative acylamino groups are phenoxyacetamido, 4-cyanophenoxyacetamido, 4-chlorophenoxyacetamido, 3,4-dichlorophenoxyacetamido, 2-chlorophenoxyacetamido, 4-methoxyphenoxyacetamido, 2-ethoxyphenoxyacetamido, 3,4-dimethylphenoxyacetamido, 4-isopropylphenoxyacetamido, 3-cyanophenoxyacetamido, 3-nitrophenoxyacetamido and like substituted phenoxyacetamido groups.

Illustrative of the acylamino groups when $R_3$ is a substituted arylalkyl group of the formula $$\begin{array}{c} R'''CH- \\ | \\ W \end{array}$$

and when W is protected hydroxy are 2-formyloxy-2-phenylacetamido, 2-benzyloxy-2-(4-methoxyphenyl)acetamido, 2-(4-nitrobenzyloxy)-2-(3-chlorophenyl)acetamido, 2-chloroacetoxy-2-(4-methoxyphenyl)acetamido, 2-benzyloxy-2-phenylacetamido, 2-trimethylsilyloxy-2-(4-chlorophenyl)acetamido, 2-benzhydryloxy-2-phenylacetamido and like groups. Representative of such groups when W is protected amino are 2-(4-nitrobenzyloxycarbonylamino)-2-(2-thienyl)acetamido, 2-(2,2,2-trichloroethoxycarbonylamino)-2-phenylacetamido, 2-chloroacetamido-2-(1,4-cyclohexadien-1-yl)acetamido, 2-(4-methoxybenzyloxycarbonylamino)-2-(4-methoxyphenyl)acetamido, 2-benzhydryloxycarbonylamino-2-(3-thienyl)acetamido, 2-(4-nitrobenzyloxycarbonyl)amino-2-phenylacetamido, and like groups.

Exemplary of the acylamino group

when $R_3$ is a heteroarylmethyl group of the formula $R''''—CH_2—$ are 2-thienylacetamido, 3-thienylacetamido, 2-furylacetamido, a 2-thiazolylacetamido group of the formula

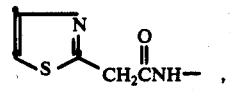

a 1-tetrazolylacetamido group of the formula

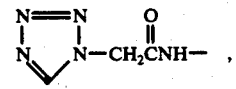

a 5-tetrazolylacetamido group of the formula

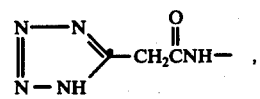

or a 3-(2-chlorophenyl)-5-methylisoxazol-4-ylamido group of the formula

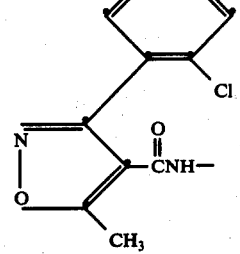

Preferred acylamino groups include formamido, acetamido, 4-nitrobenzyloxycarbonylamino, phenoxyacetamido, phenylacetamido and 2-thienylacetamido. Phenylacetamido and phenoxyacetamido are most preferred.

In general, the process of the present invention is directed to the preparation of 7-alkoxy-3-bromomethylcephem compounds by the reaction of 3-exomethylenecephams with an alkoxide base in the presence of a positive brominating agent.

The nature of the 7-alkoxy substituent on the procuct cephems is determined by the particular primary alkoxide base employed in the process. Thus, for example when lithium ethoxide is employed, a 7-ethoxy-3-halomethylcephem is produced.

The starting materials for the process of the present invention, 3-exomethylenecephams, were first disclosed as a generic class in U.S. Pat. No. 3,275,626. 7-Amino and 7-acylamino 3-exomethylenecephams can be prepared by the electroreduction (pH 2 -7) of the corresponding cephalosporin compounds having a 3-substituted methyl group such as acyloxymethyl, acylthiomethyl or quarternary ammonium methyl (U.S. Pat. No. 3,792,995). Alternatively the exomethylenecepham starting materials for the present invention can be prepared in accordance with the procedure of R. R. Chauvette and P. A. Pennington in the *Journal of Organic Chemistry*, 38, 2994 (1973) in which 3-methylenecephams are prepared from cephalosporanic acids by first treating the cephalosporanic acids with selected sulfur nucleophiles such as thiourea, thiobenzoic acid, potassium ethyl xanthate or sodium thiosulfate and then reducing the respective product, $C_3$-(substituted)thiomethyl cephem derivatives, with either Raney nickel in aqueous ethanol or zinc in formic acid-dimethylformamide. Cephalosporanic acid derivatives have also been converted to 3-exomethylenecephams on treatment with chromium (II) salts in aqueous media [M. Ochiai et al., *J. Chem. Soc. Chemical Communications*, 800 (1972)]. The 3-exomethylene cepham sulfoxide starting materials for the process of the present invention are prepared by oxidation of the corresponding sulfides with an equivalent amount of methachloroperbenzoic acid.

Although the manner in which the reactants for the process of this invention are combined is not critical, it is most preferred that the base is not contacted with the exomethylenecepham starting material without the halogenating agent being present. It should be noted, however, that the bases employed in the process of this invention will react with the exomethylenecepham in the absence of halogenating agents, at varying rates depending on the reaction temperature, to provide desacetoxymethylcephalosporins. Such conversions have been reported in the chemical literature [R. R. Chauvette and P. A. Pennington, *Journal of Organic Chemistry*, 38, 2994 (1973)]. If the base and the exomethylenecepham are combined, it is therefore preferred that the brominating agent be present in the mixture or that it be added immediately thereafter. The conversion of 3-exomethylenecephams to 3-halomethylcephems is typically carried out by adding a solution of the substrate 3-exomethylenecepham to a stirred solution of an alkali metal salt of a $C_1$–$C_7$ primary alcohol and the positive brominating agent in an inert organic solvent.

Any of a wide variety of inert organic solvents may be employed as the medium for the halogenation process of this invention. By "inert organic solvent" is meant an organic solvent which, under the conditions of the process, does not enter into any appreciable reaction with either the reactants or the products. A dry aprotic organic solvent is preferred. Trace amounts of water such as that found in commercially dried solvents, can be tolerated; however, it is generally preferred that the process of this invention, be carried out under anhydrous conditions. Suitable solvents include, for example, aromatic hydrocarbons such as benzene, chlorobenzene, toluene, ethylbenzene, xylene and the like; halogenated aliphatic hydrocarbons such as chloroform, methylene chloride, carbon tetrachloride, 1,2-dichloroethane (ethylene chloride), 1,1,2,-trichloroethane, 1,1-dibromo-2-chloroethane, and the like; aliphatic nitriles such as acetonitrile or propionitrile; esters such as ethyl acetate, butyl acetate, and the like; ethers such as 1,4-dioxane, tetrahydrofuran, diethyl ether, dimethoxyethane and the like; amides such as N,N-dimethylformamide, N,N-dimethylacetamide or hexamethylphosphoric triamide (HMPA); and any other appropriate aprotic solvents. Preferred solvents or solvent mixtures are those having a freezing point below about −10° C. Highly preferred solvents for the process of the present invention are methylene chloride, chloroform, 1,2-dichloroethane and tetrahydrofuran. Tetrahydrofuran is most preferred.

Suitable bases which can be employed to effectuate the conversion of the process of this invention are alkali metal salts of primary $C_1$–$C_7$ alcohols. The term "alkali metal salts of primary $C_1$–$C_7$ alcohols" includes the sodium, potassium, and lithium salts of primary $C_1$–$C_7$ alcohols such as methanol, ethanol, n-propanol, benzyl alcohol, n-hexanol and like alcohols. Exemplary of such alkoxide bases suitable for the process of this invention are lithium methoxide, sodium methoxide, potassium ethoxide, sodium benzyloxide, lithium ethoxide, sodium n-propoxide, and like sodium, lithium and potassium salts. The preferred of the aforementioned bases to be employed in the process of this invention are the alkali metal salts of methanol or ethanol. Lithium salts thereof are more preferred; lithium methoxide is most preferred.

The $C_7$-alkoxylation-$C_3'$-bromination of the present invention is accomplished by reacting an exomethylenecepham with from 4 to about 8 equivalents of an alkali metal salt of a primary $C_1$–$C_7$ alcohol in the presence of from 4 to about 8 equivalents of a positive brominating agent. The product from this conversion of the process of the present invention is a 7-alkoxy-3-bromomethylcephem. The best yields in this particular conversion have been found when about 8 equivalents each of an alkoxide base and a brominating agent per equivalent of cepham substrate have been employed in conjunction with a halogen quenching agent, the nature of which is discussed hereinbelow.

The use of lithium methoxide and tert-butyl hypochlorite under reaction conditions similar to those described for the process of this invention, to effectuate methoxylation of the C-7 position in cephalosporins and the C-6 position in penicillins has been described in the recent chemical literature [G. A. Koppel and R. E. Koehler, *Journal of the American Chemical Society*, 95, 2403 (1973)].

The process of the present invention is carried out at a temperature ranging from about −80° C. to about 0° C. Preferably the process is carried out between about −80° C. and about −20° C.; however, where the side chain moiety of the cepham substrate is also subject to halogenation, especially bromination, the process of this invention is preferably carried out at a temperature of less than about −40° C. Such halogen-reactive C-7 side chains include 2-thienylacetamido, 3-thienylacetamido, 2-furylacetamido and like groups. In addition to performing the process of this invention at lower temperature when the starting material has such halogen-reactive substituents, it is necessary that a halogen quenching agent also be added to the reaction mixture before it is allowed to warm above about 0° C. The halogen quenching agent is added to destroy any excess brominating reagent at the lower reaction temperature, thereby eliminating or substantially decreasing the likelihood of undesirable side reactions between any excess brominating agent and halogen-reactive side chains present on the starting materials and the product 7-alkoxy-3-bromomethylcephems.

The term "halogen quenching agent" as employed hereinabove in describing the process of this invention refers to those reagents not reactive with the cepham starting materials nor the cephem products of the process of this invention, but capable of reacting with the brominating reagent, thereby rendering the brominating reagent or more accurately any excess thereof unreactive toward the 3-bromomethylcephem products of the process of this invention. Typically halogen quenching agents employed in the process of this invention are halogen reducing agents, however, other quenching agents with which the excess halogenating agent will react preferentially (versus further reaction with the 3-bromomethylcephem products) are suitable. Suitable halogen quenching agents include di($C_1$–$C_6$ alkyl)sulfides, tri($C_1$–$C_6$ alkyl)phosphites, olefins, acetylenes, and like organic halogen reactive agents. Likewise aqueous solutions of known reducing-inorganic salts such as bisulfite, metabisulfite, thiosulfate and dithionite salts can be successfully employed.

Exemplary of sulfide and phosphite halogen quenching agents useful in the process of the present invention are dimethylsulfide, di-n-propylsulfide, dicyclohexylsulfide, methylethylsulfide, trimethylphosphite, triethylphosphite, and tri-n-butylphosphite. Representative of the olefins and acetylenes which can be employed as quenching agents in the process of this invention include diethylacetylene dicarboxylate; vinylethers including methylvinylether, ethyl vinylether and like alkylvinyl ethers; and vinylesters like vinyl acetate. Exemplary of suitable reducing inorganic salts are sodium bisulfite, potassium bisulfite, sodium metabisulfite, potassium thiosulfate, sodium dithionite and like reducing salts.

The halogen quenching agents are typically added to the reaction mixture after the bromination-alkoxylation reaction has reached completion, as detected, for example by comparative thin-layer chromatography, and preferably before the reaction mixture is allowed to warm above about 0° C. When aqueous solutions of the aforedescribed reducing inorganic salts are employed as quenching agents, their addition typically constitutes the first step in the workup of the reaction mixture. However, where the reaction temperature is less than about −20° C., the aforedescribed organic halogen quenching agents may be added to the reaction mixture before the halogenation reaction is initiated. Thus, for example, 4'-methoxybenzyl 7-(2-thienylacetamido)-7-methoxy-3-bromomethyl-3-cephem-4-carboxylate can be prepared by adding a solution of 1 equivalent of 4'-methoxybenzyl 7-(2-thienylacetamido)-3-methylenecepham-4-carboxylate in tetrahydrofuran to a solution of 8 equivalents lithium methoxide, 8 equivalents of bromine, and 8 equivalents of trimethylphosphite in tetrahydrofuran at −60° C. The trimethylphosphite is unreactive to the brominating agent at the lower reaction temperature, but as the reaction mixture is allowed to warm above the reaction temperature after the methoxylation-bromination is complete, the trimethylphosphite only then reacts with the excess bromine in the mixture.

The major product of the aforedescribed example performed without the presence of a halogen quenching agent is 4'-methoxybenzyl 7-[2-(5-bromothienyl)acetamido]-7-methoxy-3-bromomethyl-3-cephem-4-carboxylate. It should be noted that although side chain halogenation is generally undesirable, the 3-bromomethylcephem products produced in such reactions are none the less useful in preparing other 3-bromomethylcephem compounds. Thus, for example, the 4'-methoxybenzyl 7-[2-(5-bromothienyl)acetamido]-7-methoxy-3-bromomethyl-3-cephem-4-carboxylate can be cleaved under essentially non-aqueous side chain cleavage conditions ($PCl_5$, pyridine/methanol) to provide the corresponding nucleus ester 4'-methoxybenzyl 7-amino-7-methoxy-3-bromomethyl-3-cephem-4-carboxylate which thereafter can be reacylated as desired. Therefore, conversions of 3-methylenecephams to 7-alkoxy-3-bromomethylcephems having, in addition, halogen substituted side chains, are also to be considered within the scope of the present invention.

The amount of quenching agent employed is not critical so long as a sufficient quantity is added to render inactive the excess brominating agent in the reaction mixture. Generally, a 1–10 fold excess or more of the halogen quenching agent is employed.

Although the use of halogen quenching agents in the process of the present invention has been found necessary only in the instances where the substrate exomethylenecepham has a halogen-reactive side chain, higher yields of product 3-bromomethylcephems are generally obtained when such quenching agents are employed. Typically, therefore, halogen quenching agents are employed in the process of the present invention, even where the substrate exomethylenecepham does not have a halogen-reactive side chain. The general use of halogen quenching agents in the process of this invention is therefore preferred.

It is also preferred in the process of the present invention to add an excess of a protic acid to the reaction mixture before it is allowed to warm above about 0° C. This optional but preferred procedure serves to preclude any undesirable side reactions between the 7-alkoxy-3-bromomethylcephem product and the excess base in the reaction mixture. Both organic and inorganic protic acids are suitable. Representative of such are formic acid, acetic acid, propionic acid, trifluoroacetic acid, methanesulfonic acid, p-toluenesulfonic acid, hydrochloric acid, and like organic and inorganic protic acids.

The time of reaction will range generally from about 5 minutes to about 1 hour with the reaction time being dependent to some extent upon the particular reactants, the solvents employed, and the temperature at which the reaction is carried out. Usually the reaction will be complete after the reactants have been maintained in contact at the preferred temperatures for about 5 to 15 minutes. The reaction mixture can easily be monitored, for example, by comparative thin-layer chromatography, to determine when the bromination-alkoxylation reaction has reached completion.

Exemplary of the conversions effectuated by employing the process of the present invention are the following:

tert-butyl 7-phenylacetamido-3-methylenecepham-4-carboxylate to tert-butyl 7-phenylacetamido-7-ethoxy-3-bromomethyl-3-cephem-4-carboxylate using lithium ethoxide and tert-butyl hypobromite;

benzyl 7-(4-nitrobenzyloxycarbonylamino)-3-methylenecepham-4-carboxylate to benzyl 7-(4-nitrobenzyloxycarbonylamino)-7-methoxy-3-bromomethyl-3-cephem-4-carboxylate using lithium methoxide and tert-butyl hypobromite;

4'-nitrobenzyl 7-acetamido-3-methylenecepham-4-carboxylate 1-oxide to 4'-nitrobenzyl 7-acetamido-7-n-propoxy-3-bromomethyl-3-cephem-4-carboxylate-1-oxide using bromine and sodium n-propoxide;

2',2',2'-trichloroethyl 7-(2-phenyl-2-benzyloxyacetamido)-3-methylenecepham-4-carboxylate to 2',2',2'-trichloroethyl-7-(2-phenyl-2-benzyloxyacetamido)-7-methoxy-3-bromomethyl-3-cephem-4-carboxylate using bromine and sodium methoxide;

benzhydryl 7-formamido-3-methylenecepham-4-carboxylate to benzhydryl 7-formamido-7-methoxy-3-bromomethyl-3-cephem-4-carboxylate using DBU hydrobromide perbromide and lithium methoxide;

2'-iodoethyl 7-(2-formyloxy-2-phenylacetamido)-3-methylenecepham-4-carboxylate to 2'-iodoethyl 7-(2-formyloxy-2-phenylacetamido)-7-benzyloxy-3-bromomethyl-3-cephem-4-carboxylate using tert-butyl hypobromite and lithium benzyloxide;

4'-methoxybenzyl 7-phenoxyacetamido-3-methylenecepham-4-carboxylate to 4'-methoxybenzyl-7-phenoxyacetamido-7-methoxy-3-bromomethyl-3-cephem-4-carboxylate using lithium methoxide and bromine;

2',2',2'-trichloroethyl 7-[2-(4-nitrobenzyloxycarbonylamino)-2-phenylacetamido]-3-methylenecepham-4-carboxylate to 2',2',2'-trichloroethyl 7-[2-(4-nitrobenzyloxycarbonylamino)-2-phenylacetamido]-7-propoxy-3-bromomethyl-3-cephem-4-carboxylate using lithium propoxide and tert-butyl hypobromite;

4'-nitrobenzyl 7-(2-furylacetamido)-3-methylenecepham-4-carboxylate to 4'-nitrobenzyl 7-(2-furylacetamido)-7-methoxy-3-bromomethyl-3-cephem-4-carboxylate using bromine, lithium methoxide and trimethylphosphite;

tert-butyl 7-(4-chlorophenylacetamido)-3-methylenecepham-4-carboxylate to tert-butyl 7-(4-chlorophenylacetamido)-7-ethoxy-3-bromomethyl-3-cepham-4-carboxylate using lithium ethoxide and bromine; and 4'-methoxybenzyl 7-chloroacetamido-3-methylenecepham-4-carboxylate to 4'-methoxybenzyl 7-chloroacetamido-7-ethoxy-3-chloromethyl-3-cephem-4-carboxylate using lithium ethoxide and iodine monobromide.

The products produced in accordance with the process of this invention can be isolated and purified by employing conventional experimental techniques. These include chromatographic separation, filtration, crystallization and recrystallization.

The product 3-bromomethylcephem compounds of the process of this invention are useful as intermediates in the preparation of antibiotics. The sulfoxides can be reduced by known procedures, typically with phosphorus tribromide or phosphorus trichloride in dimethylformamide to provide the corresponding 3-bromomethylcephems. The 3-bromomethylcephem esters are converted to active antibiotics by cleavage of the ester function (U.S. Pat. No. 3,658,799). Deesterification can be achieved, depending on the nature of the ester group, by any one of several recognized procedures, including (1) treatment with an acid such as trifluoroacetic acid, formic acid, hydrochloric acid or the like; (2) treatment with zinc and an acid such as formic acid, acetic acid or hydrochloric acid; or (3) hydrogenation in the presence of palladium, platinum, rhodium, or a compound thereof, in suspension, or on a carrier such as barium sulfate, carbon, or alumina.

Alternatively the 7-alkoxy-3-bromomethylcephems can be converted to other 3-(substituted)methylcephem compounds by nucleophilic displacement of the bromo moiety. Such is a procedure recognized by those skilled in the art for preparing a wide variety of known active 3-heteroarylthiomethyl cephem compounds. The 7-alkoxy-3-bromomethylcephem compounds provided by the process of the present invention are also key intermediates for the preparation of known clinically significant cephem antibiotics. Thus, for example, benzhydryl 7-(2-thienylacetamido)-7-methoxy-3-bromomethyl-3-cephem-4-carboxylate can be reacted with calcium carbamate, and the ester group can be removed to provide the known antibiotic cefoxitin.

The following examples are provided to further illustrate the present invention. It is not intended that this invention be limited in scope by reason of any of these examples. In the following examples nuclear magnetic resonance spectra were obtained on a Varian Associates T-60 Spectrometer using tetramethylsilane as the reference standard. The chemical shifts are expressed in $\delta$ values in parts per million (ppm) and coupling constants (J) are expressed in cycles per second.

EXAMPLE 1

4'-Nitrobenzyl 7-phenoxyacetamido-7-methoxy-3-bromoethyl-3-cephem-4-carboxylate

To a solution of 0.256 g. of dry methanol in 15 ml. of THF at $-80°$ C. was added 4.17 of 1.85 n. methyl lithium in THF. The mixture was stirred for 5 minutes after which time was added 0.44 ml. of bromine. To the resulting mixture was added a solution of 0.483 g. of 4'-nitrobenzyl 7-phenoxyacetamido-3-methylenecepham-4-carboxylate in 4 ml. of tetrahydrofuran. After the reaction mixture was allowed to warm to 0° C. and stirred for 15 minutes at that temperature, 3 ml. of trimethylphosphite were added. The reaction mixture was then evaporated in vacuo and residue thereby obtained was dissolved in methylene chloride. The resulting solution of the residue was washed successively three times with a saturated solution of sodium chloride, once with a dilute solution of sodium thiosulfate, twice with a solution of sodium bicarbonate, and thereafter once with a saturated solution of sodium chloride. The washed solution was then dried and evaporated in vacuo to give an impure product which was purified by preparative thin-layer chromatography using a benzene/ethyl acetate gradient to provide 140 mg. of the title product:

nmr (CDCl$_3$) $\delta$ 3.53 (s, 5, C$_2$—H and C$_6$—OCH$_3$), 4.42 (bs, 2, C$_3$—C$H$Br), 4.62 (s, 2, side chain CH$_2$), 5.14 (s, 1, C$_6$—H), 5.42 (s, 2, ester CH$_2$), 6.8–8.4 (ArH).

The structure of the product was confirmed by comparison with an authentic sample of p-nitrobenzyl 7-phenoxy-acetamido-7-methoxy-3-bromomethyl-3-cephem-4-carboxylate prepared by 7-methoxylation of p-nitrobenzyl 7-phenoxyacetamido-3-bromomethyl-3-cephem-4-carboxylate via its reaction with lithium methoxide and t-butyl hypochlorite in tetrahydrofuran at $-80°$ C.

EXAMPLE 2

Benzhydryl 7-(2-thienylacetamido)-7-methoxy-3-bromomethyl-3-cephem-4-carboxylate.

In accordance with the procedures described by Example 1, benzhydryl 7-(2-thienylacetamido)-3-methylenecepham-4-carboxylate was reacted with 8 equivalents of lithium methoxide in tetrahydrofuran in the presence of 8 equivalents of bromine at $-80°$ C. to provide the title product:

nmr (CDCl$_3$) $\delta$ 3.41 (bs, 2, C$_2$—H), 3.46 (s, 3, C$_7$—OCH$_3$), 3.83 (s, 2, side chain CH$_2$), 4.20, 4.34 (ABq, 2, C$_3$—CH$_2$Br), 5.06 (s, 1, C$_6$—H), and 6.8–7.6 (m, 14, ArH and benzhydryl C$H$).

I claim:

1. A process for preparing a 3-bromomethylcephem compound of the formula

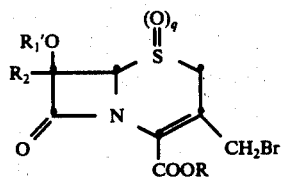

which comprises reacting a compound of the formula

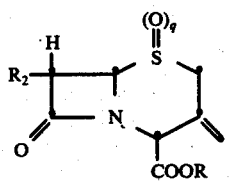

with from about 4 to about 8 equivalents of an alkali metal salt of a $C_1$-$C_7$ primary alcohol of the formula $R_1'OH$ in the presence of about 4 to about 8 equivalents of a positive brominating agent selected from the group consisting of bromine, DBU hydrobromide perbromide, iodine monobromide and tert-butyl hypobromite in an inert organic solvent at a temperature of $-80°$ to about $-20°$ C. wherein in the above formulae $q$ is 1 or 0;

R is a carboxylic acid protecting group;

$R_1'$ is primary $C_1$-$C_6$ alkyl or benzyl; and $R_2$ is an amido group of the formula

wherein $R_3$ is
a. hydrogen, $C_1$-$C_3$ alkyl, halomethyl, 3-(2-chlorophenyl)-5-methylisoxazol-4-yl or 4-protected amino-4-protected carboxybutyl;
b. benzyloxy, 4-nitrobenzyloxy, 2,2,2-trichloroethoxy, tert-butoxy, or 4-methoxybenzyloxy;
c. the group —R" wherein R" is 1,4-cyclohexadienyl, phenyl or phenyl substituted with 1 or 2 substituents independently selected from the group consisting of halo, protected hydroxy, nitro, cyano, trifluoromethyl, $C_1$-$C_3$ alkyl, and $C_1$-$C_7$ alkoxy;
d. an arylalkyl group of the formula

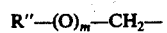

wherein R" is as defined above, and $m$ is 0 or 1;
e. a substituted arylalkyl group of the formula

wherein R'" is R" as defined above, 2-thienyl or 3-thienyl, and W is protected hydroxy or protected amino; or
f. a heteroarylmethyl group of the formula

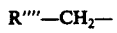

wherein R"" is 2-thienyl, 3-thienyl, 2-furyl, 2-thiazolyl, 5-tetrazolyl, 1-tetrazolyl, or 4-isoxazolyl;
with the limitation that when R'" or R""is 2thienyl, 3-thienyl or 2-furyl the reaction is carried out at a temperature below about $-40°$ C. and a halogen quenching agent is added before the mixture is allowed to warm above about 0° C.

2. The process of claim 1 wherein R is methyl, tert-butyl, benzyl, 4-methoxybenzyl, $C_2$-$C_6$ alkanoyloxymethyl, 2-iodoethyl, 4-nitrobenzyl, benzhydryl, phenacyl, p-halophenacyl, 2,2,2-trichloroethyl, tri($C_1$-$C_3$ alkyl)silyl and succinimidomethyl.

3. The process of claim 2 wherein $q$ is 0.

4. The process of claim 3 wherein the base is a lithium salt of a primary $C_1$-$C_7$ alcohol of the formula $R_1'OH$.

5. The process of claim 4 wherein, additionally, before the reaction mixture is allowed to warm above about 0°, an excess of protic acid is added to the reaction mixture.

6. The process of claim 3 wherein the brominating agent is bromine.

7. The process of claim 3 wherein the halogen quenching agent is a di($C_1$-$C_6$ alkyl)sulfide, a tri($C_1$-$C_6$ alkyl)phosphite, diethylacetylene dicarboxylate, methylvinylether, ethylvinylether, vinylacetate or a bisulfite, metabisulfite, thiosulfate or dithionate salt.

8. The process of claim 3 wherein R'" or R"" is other than 2-thienyl, 3-thienyl, or 2-furyl and wherein, additionally, a halogen quenching agent is added to the reaction mixture before the reaction mixture is allowed to warm above about 0° C.

9. The process of claim 8 wherein the halogen quenching agent is a halogen reducing agent.

10. The process of claim 8 wherein the halogen quenching agent is a water soluble bisulfite, metabisulfite, thiosulfate or dithionite inorganic salt.

11. The process of claim 8 wherein the halogen quenching agent is dimethylsulfide, di-n-propyl sulfide, dicyclohexyl sulfide, methyl ethyl sulfide, trimethylphosphite, triethylphosphite or tri-n-butylphosphite.

12. The process of claim 11 wherein $R_3$ is an arylalkyl group of the formula R"—(O)$_m$—CH$_2$— and wherein the exomethylenecepham carboxylate starting material is added to a solution of about 8 equivalents of bromine, about 8 equivalents of lithium methoxide and about 10 equivalents of trimethylphosphite per equivalent of exomethylenecepham in tetrahydrofuran at about $-70°$ C. and wherein an excess of a protic acid is added to the reaction mixture before it is allowed to warm above about 0° C.

* * * * *